US006215038B1

(12) United States Patent
Davis et al.

(10) Patent No.: US 6,215,038 B1
(45) Date of Patent: Apr. 10, 2001

(54) DIAPER WITH OSMOTIC PRESSURE CONTROL

(75) Inventors: James Arthur Davis; Pamela Jean Mayberry, both of Roswell; Michael Tod Morman, Alpharetta, all of GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/364,214

(22) Filed: Jul. 29, 1999

Related U.S. Application Data

(63) Continuation-in-part of application No. 09/322,612, filed on May 28, 1999, now abandoned.

(51) Int. Cl.$^7$ ............................................. A61F 13/15
(52) U.S. Cl. ........................................ 604/367; 604/385.23
(58) Field of Search .............................. 604/367, 385.23

(56) References Cited

U.S. PATENT DOCUMENTS

| | | | | |
|---|---|---|---|---|
| 3,802,909 | * | 4/1974 | Rockett et al. | 117/100 |
| 3,982,983 | | 9/1976 | Abraham et al. | 156/154 |
| 4,036,668 | | 7/1977 | Brandon | 148/6.35 |
| 4,061,846 | * | 12/1977 | Gross et al. | 526/16 |
| 4,199,068 | * | 4/1980 | Weitzner | 211/49 |
| 4,272,422 | | 6/1981 | Tanaka | 260/29.6 |
| 4,335,722 | * | 6/1982 | Jackson | 128/285 |
| 4,345,048 | | 8/1982 | Friedli et al. | 525/192 |
| 4,540,731 | | 9/1985 | Gilvary et al. | 524/269 |
| 4,616,060 | | 10/1986 | Killgoar, Jr. | 524/574 |
| 4,645,791 | | 2/1987 | Theodore et al. | 524/490 |
| 4,820,293 | * | 4/1989 | Kamme | 604/368 |
| 4,853,428 | | 8/1989 | Theodore et al. | 524/491 |
| 5,082,723 | | 1/1992 | Gross et al. | 428/283 |
| 5,108,383 | | 4/1992 | White | 604/368 |
| 5,183,872 | * | 2/1993 | Heidel et al. | 527/300 |
| 5,330,459 | * | 7/1994 | Lavon et al. | 604/385.1 |
| 5,487,736 | * | 1/1996 | Van Phan | 604/368 |
| 5,562,649 | | 10/1996 | Chauvette et al. | 604/375 |
| 5,604,200 | | 2/1997 | Taylor-McCord | 514/8 |
| 5,693,411 | * | 12/1997 | Hansen et al. | 428/283 |
| 5,713,881 | * | 2/1998 | Rezai et al. | 604/368 |
| 5,925,439 | * | 7/1999 | Haubach | 428/178 |
| 5,928,665 | * | 7/1999 | Cercone | 424/445 |
| 5,976,995 | | 11/1999 | Palmer, Jr. | 442/118 |
| 6,001,935 | | 12/1999 | Palmer, Jr. | 525/437 |
| 6,004,307 | * | 12/1999 | Colon et al. | 604/385.1 |
| 6,018,093 | * | 1/2000 | Roe et al. | 604/367 |

FOREIGN PATENT DOCUMENTS

99/22684   5/1999  (WO) .............................. A61F/13/15

* cited by examiner

*Primary Examiner*—Dennis Ruhl
*Assistant Examiner*—Paul Shanoski
(74) *Attorney, Agent, or Firm*—James B. Robinson

(57) ABSTRACT

There is provided a personal care product having an osmolality changing agent incorporated into it which achieves the objects of this invention. The agent can reduce skin hydration significantly by increasing the osmolality of a solution outside of, but in contact with, the skin, in order to cause water to move across the skin cellular boundary to dilute the solution. Such a material is preferably compatible with modern fiber forming processes like spunbonding and meltblowing. The reduction of skin hydration may reduce redness and irritation due to contact with fluids.

15 Claims, No Drawings

DIAPER WITH OSMOTIC PRESSURE CONTROL

This case is a continuation-in-part of U.S. patent application Ser. No. 09/322,612 filed May 28, 1999, now abandoned, with the same inventors and assignee, and claims priority therefrom.

FIELD OF THE INVENTION

This invention relates to absorbent articles, particularly absorbent structures that are useful in personal care products such as disposable diapers, incontinence guards, childcare training pants, feminine hygiene products and the like. (The reference to "diapers" in the title is merely illustrative).

BACKGROUND OF THE INVENTION

Personal care products include absorbent articles like diapers, training pants, incontinence devices, feminine hygiene products and the like. These products are designed to absorb and contain body exudates and are generally single-use or disposable items which are discarded after a relatively short period of use—usually a period of hours—and are not intended to be washed and reused. Such products are placed against or in proximity to the wearer's body to absorb and contain various exudates discharged from the body. All of these products typically include a liquid permeable bodyside liner or cover, a liquid impermeable outer cover or backsheet, and an absorbent structure disposed between the bodyside liner and outer cover. The liquid impermeable outer cover may be breathable, i.e., permeable to water vapor.

It has been found that urination can occur at rates as high as 15 to 20 milliliters per second and at velocities as high as 280 centimeters per second. The volume of urine released per occurrence can vary from about a nominal amount to about 100 ml. It's important for the absorbent article to rapidly uptake liquid to avoid excessive pooling of liquid on the body-facing surface of the bodyside liner in order to avoid leakage. Even if absorbed, however, any liquid in the article contributes to the overall humidity near the wearer' skin, causing discomfort and potential skin health problems due to skin hydration.

The problem of excessive humidity near the skin in an absorbent article has been addressed in the art through a number of means. U.S. Pat. No. 5,137,525 for example, uses mechanical means to increase airflow in the article. Breathable outer covers allow air and water vapor diffusion and have been mentioned previously. Osmotic agents have been investigated for use in personal care products to a minor extent. U.S. Pat. No. 5,108,383 to Lloyd White, dated Apr. 28, 1992, for example, discusses the use of materials such as sodium chloride, sugars and other water soluble salts as osmotic promoters in diapers and the like. The agent is enclosed in a film packet or bag that is placed in the article to encourage the absorption of large quantities of liquid. White teaches that the packet, which could also include wood fluff and other absorbing materials, outer non-absorbing sheets, fasteners and the like, is placed in a composite structure designed to pick up and retain fluids. The osmotic agent does not leave the packet but encourages the flow of liquid into the packet by osmotic pressure so the packet functions like a layer of superabsorbent, absorbing large volumes of fluid.

Despite these attempts, the need exists for further improvement in the reduction of skin hydration within absorbent articles. In particular, there is a need for agents that can remove water from the skin or reduce water absorption into the skin. The present invention provides for such reduced skin hydration within an ab sorbent article. More particularly, the invention relates to absorbent articles that reduce the hydration of the skin by modifying osmotic pressure through the use of agents.

SUMMARY OF THE INVENTION

A personal care product having an osmolality changing agent incorporated into it achieves the objects of this invention. The osmolality changing agent functions by dissolving in the water (urine) released by the wearer, thus increasing the concentration of the agent in the water in the product and causing molecular water to pass outwardly through the skin cellular boundary to dilute the solution by osmotic action. The agent can reduce skin hydration significantly. Since intracellular fluid (fluid within cells) has an osmolality of about 300 milliosmoles per kilogram (mOs/kg), a solution outside of the cell, e.g., outside of the body, must have an osmolality of greater than about 300 mOs/kg in order to cause water to move from the interior of the cell to the exterior. Such a material may preferably be used in modern fiber forming processes like spunbonding and meltblowing. The reduction of skin hydration may reduce skin redness and irritation.

DEFINITIONS

"Disposable" includes being disposed of after usually a single use and not intended to be washed and reused.

"Layer" when used in the singular can have the dual meaning of a single element or a plurality of elements.

"Liquid" means a nongaseous substance and/or material that flows and can assume the interior shape of a container into which it is poured or placed.

"Liquid communication" means that liquid such as urine is able to travel from one location to another location.

"Particles" refers to any geometric form such as, but not limited to, spherical grains, cylindrical fibers or strands, or the like.

"Spunbonded fibers" refers to small diameter fibers which are formed by extruding molten thermoplastic material as filaments from a plurality of fine capillaries of a spinneret. Such a process is disclosed in, for example, U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. The fibers may also have shapes such as those described in U.S. Pat. No. 5,277,976 to Hogle et al., U.S. Pat. No. 5,466,410 to Hills and U.S Pat. No. 5,069,970 and 5,057,368 to Largman et al., which describe fibers with unconventional shapes.

"Meltblown fibers" means fibers formed by extruding a molten thermoplastic material through a plurality of fine die capillaries as molten filaments into converging high velocity, usually hot, gas (e.g. air) streams which attenuate the filaments of molten thermoplastic material to reduce their diameter. Such a process is disclosed, for example, in U.S. Pat. No. 3,849,241. Meltblown fibers are microfibers which may be continuous or discontinuous, and are generally smaller than 10 microns in average diameter.

"Conjugate fibers" refers to fibers which have been formed from at least two polymers arranged in substantially constantly positioned distinct zones across the cross-section of the fibers and which extend continuously along the length of the fibers. Conjugate fibers are taught in U.S. Pat. No. 5,108,820 to Kaneko et al., U.S. Pat. No. 5,336,552 to Strack et al., and U.S. Pat. No. 5,382,400 to Pike et al.

"Biconstituent fibers" refers to fibers, which have been formed from at least two polymers extruded from the same extruder as a blend. Fibers of this general type are discussed in, for example, U.S. Pat. No. 5,108,827 to Gessner "Bonded carded web" refers to webs that are made from staple fibers which are sent through a combing or carding unit, which separates or breaks apart and aligns the staple fibers in the machine direction to form a generally machine direction-oriented fibrous nonwoven web. Such fibers are usually purchased in bales, which are placed in an opener/blender, or picker, which separates the fibers prior to the carding unit. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable and well-known bonding method, particularly when using conjugate staple fibers, is through-air bonding.

"Airlaying" is a well-known process by which a fibrous nonwoven layer can be formed. In the airlaying process, bundles of small fibers having typical lengths ranging from about 3 to about 19 millimeters (mm) are separated and entrained in an air supply and then deposited onto a forming screen, usually with the assistance of a vacuum supply. The randomly deposited fibers then are bonded to one another using, for example, hot air or a spray adhesive.

"Personal care product" means diapers, training pants, absorbent underpants, adult incontinence products, feminine hygiene products, wound care items like bandages, and other articles.

TEST METHODS

Armband Skin Hydration Test—The purpose of this test is to mimic the wearing of a wet diaper by a baby and to then measure the effect of the moisture on the skin. A model personal care product about 4 by 12 inches (10 by 30.5 cm) is made using typical diaper liner, absorbent and film (outercover). Leg elastic is used along the long edges. This model is stretched in length, wrapped around the forearm of a volunteer, and secured with tape. The tape is placed in the length direction of the product so it does not contact the skin. Elastic netting is stretched and placed over the model to hold it in place on the forearm. The desired amount of liquid is injected between the skin and the model. The armbands are worn for 1 hour and the skin hydration assessed using an Evaporimeter model ServoMed EP1, made by ServoMed AB in Stockholm, Sweden, by placing the Evaporimeter sensor on the skin. Evaporimeter results are reported in $g/m^2$ in two minutes.

DETAILED DESCRIPTION

Traditional absorbent systems for personal care products may be generalized as having the functions of surge control and containment (retention) or SC.

Surge control materials, the "S" in SC, are provided to quickly accept the incoming insult and either absorb, hold, channel or otherwise manage the liquid so that it does not leak outside the article. The surge layer may also be referred to as an intake layer, transfer layer, transport layer and the like. A surge material must typically be capable of handling an incoming insult of between about 60 and 100 ml at an insult volumetric flow rate of from about 5 to 20 ml/sec, for infants, for example. Containment or retention materials, the "C" in SC, must absorb the insult quickly and efficiently. They are in liquid communication with the surge layer and should be capable of pulling the liquid from the surge layer and absorbing the liquid without significant blocking of penetration of liquid further into the absorbent. Retention materials are often high rate superabsorbent materials such as blends of polyacrylate superabsorbent and fluff. These materials rapidly absorb and hold liquid.

In addition to the surge control and containment materials in traditional absorbent systems, recent work has introduced another layer interposed between the S and C layers and in liquid communication with them. This new layer is a distribution layer, producing a system with surge control, distribution and containment or "SDC".

Distribution materials, the "D" in SDC, must be capable of moving fluid from the point of initial deposition to where storage is desired. Distribution must take place at an acceptable rate such that the target insult area, generally the crotch area, is ready for the next insult. By "ready for the next insult" it is meant that sufficient liquid has been moved out of the target zone so that the next insult results in liquid absorption and runoff within acceptable volumes. The time between insults can range from just a few minutes to hours, generally depending on the age of the wearer.

Absorbent products such as, for example, diapers, generally also have a liner which goes against the wearer and a backsheet which is the most exterior layer. An absorbent product may also contain other layers as well.

The liner is sometimes referred to as a bodyside liner or topsheet and is adjacent the surge material. In the thickness direction of the article, the liner material is the layer against the wearer's skin and so the first layer in contact with liquid or other exudate from the wearer. The liner further serves to isolate the wearer's skin from the liquids held in an absorbent structure and should be compliant, soft feeling and non-irritating.

Various materials can be used in forming the bodyside liner of the present invention, including apertured plastic films, woven fabrics, nonwoven webs, porous foams, reticulated foams and the like. Nonwoven materials have been found particularly suitable for use in forming the bodyside liner. These include spunbond or meltblown webs of polyolefin, polyester, polyamide (or other like fiber forming polymer) filaments, or bonded carded webs of natural polymers (for example, rayon or cotton fibers) and/or synthetic polymers (for example, polypropylene or polyester) fibers. The nonwoven web can be surface treated with a selected amount of surfactant, such as TRITON® X-102 or ACHOVEL® surfactant in an amount between about 0.05 and 0.5 weight percent, or otherwise processed to impart the desired level of wettability and hydrophilicity. If a surfactant is used, it can be an internal additive that migrates to the surface or applied to the web by any conventional means, such as spraying, printing, dipping, brush coating and the like.

The surge layer is most typically interposed between and in intimate, liquid communicating contact with the bodyside liner and another layer such as a distribution or retention layer. The surge layer is generally subjacent the inner (unexposed) surface of bodyside liner. To further enhance liquid transfer, it can be desirable to attach the upper and/or lower surfaces of the surge layer to the liner and the distribution layer, respectively. Suitable conventional attachment techniques may be utilized, including without limitation, adhesive bonding (using water-based, solvent-based and thermally activated adhesives), thermal bonding, ultrasonic bonding, needling and pin aperturing, as well as combinations of the foregoing or other appropriate attachment methods. If, for example, the surge layer is adhesively bonded to the bodyside liner, the amount of adhesive add-on should be sufficient to provide the desired level(s) of bonding, without excessively restricting the flow of liquid from the liner into the surge layer. Various woven and nonwoven webs and foams can be used to construct a surge layer. For example, the surge layer may be a nonwoven fabric layer composed of a meltblown or spunbond web of polyolefin filaments. Such nonwoven fabric layers may include conjugate, biconstituent and homopolymer fibers of staple or other lengths and mixtures of such fibers with other types of fibers. The surge layer also can be a bonded-carded web or an airlaid web composed of natural and/or synthetic fibers. The bonded-carded web may, for example, be a powder bonded carded web, an infrared bonded carded web, or a through-air bonded carded web. Further examples of surge materials may be found in U.S. Pat. No. 5,490,846 to Ellis et al. and in U.S. Pat. No. 5,364,382 to Latimer. Surge layers may be composed of a substantially hydrophobic material, and the hydrophobic material may optionally be treated with a surfactant or otherwise processed to impart a desired level of wettability and hydrophilicity. Surge layers can have a generally uniform thickness and cross-sectional area.

A distribution layer, if present, must be capable of moving fluid from the point of initial deposition to where storage is desired. Distribution must take place at an acceptable rate such that the target insult area, generally the crotch area, is ready for the next insult. The time between insults can range from just a few minutes to hours, generally depending on the age of the wearer. Materials from which the distribution layer may be made include woven fabrics and nonwoven webs. For example, the distribution layer may be a nonwoven fabric layer composed of a meltblown or spunbond web of polyolefin, polyester, polyamide (or other web-forming polymer) filaments. Such nonwoven fabric layers may include conjugate, biconstituent and homopolymer fibers of staple or other lengths and mixtures of such fibers with other types of fibers. The distribution layer also can be a bonded-carded web, an airlaid web or a wetlaid pulp structure composed of natural and/or synthetic fibers or a combination thereof.

Retention materials are typically cellulosic materials or superabsorbents or mixtures thereof. Such materials are usually designed to quickly absorb liquids and hold them without, usually without release. Superabsorbents are commercially available from a number of manufactures including Dow Chemical Company of Midland, Mich. and Stockhausen Corporation of Greensboro, N.C. Retention materials may be zoned and their compositions chosen to move liquids away from the target zone to more remote storage locations. Such a design more efficiently uses the entire absorbent article.

The backsheet is sometimes referred to as the outer cover and is the farthest layer from the wearer. The outer cover is typically formed of a thin thermoplastic film, such as polyethylene film, which is substantially impermeable to liquid. The outer cover functions to prevent body exudates contained in an absorbent structure from wetting or soiling the wearer's clothing, bedding, or other materials contacting the diaper. The outer cover may be, for example, a polyethylene film having an initial thickness of from about 0.5 mil (0.012 millimeter) to about 5.0 mil (0.12 millimeter). The polymer film outer cover may be embossed and/or matte finished to provide a more aesthetically pleasing appearance. Other alternative constructions for outer cover include woven or nonwoven fibrous webs that have been constructed or treated to impart the desired level of liquid impermeability, or laminates formed of a woven or nonwoven fabric and thermoplastic film. The outer cover may optionally be composed of a vapor or gas permeable, "breathable" material, that is permeable to vapors or gas yet substantially impermeable to liquid. Backings may also serve the function of a mating member for mechanical fasteners, in the case, for example, where a nonwoven fabric is the outer surface.

Despite the advantages of modern surge, distribution and retention materials, it has been found that a small amount of liquid can still remain in contact with the skin for some time after urination into a personal care product. The inventors have found that the incorporation of an osmolality changing agent into a personal care article like a diaper can reduce skin hydration significantly. It's believed this will have the effect of reducing redness and irritation of the skin.

Intracellular bodily fluid (fluid within cells) and extracellular bodily fluid (fluid outside the cell) have an osmolality of about 300 milliosmoles per kilogram (mOs/kg) according to the Textbook of Medical Physiology, (sixth edition, ISBN 0-7216-4394-9, published by W.B. Saunders Company, Philadelphia, Pa., at page 49). Another source reports the extracellular fluid as having slightly lower values of about 275–290 mOs/kg (Harrison's Principles of Internal Medicine, $14^{th}$ edition, volume one, ISBN 0-07-020292-3, published by McGraw-Hill, New York, N.Y., at page 266). Therefore, a solution outside of the body, must have an osmolality of greater than about 300 mOs/kg in order to prevent water from moving from the exterior of the cell to the interior, thus achieving the objective of decreasing skin cell hydration. Any osmolality changing agent that raises the osmolality of the fluid adjacent the skin above about 300 mOs/kg should result in positive effects on skin hydration and thus on skin redness and irritation.

The osmolality changing agent functions by dissolving in the water (urine) released by the wearer, thus increasing the concentration of the agent in the water. This increases the osmolality of the liquid in the personal care product to a value greater than that of the intracellular fluid. This causes water to pass outwardly through the cellular boundary (wall) of the wearer's skin to dilute the solution. This process, known, as osmosis, is the tendency of a fluid, e.g. water, to pass through a semi-permeable membrane, such as the wall of a living skin cell, into a solution of higher concentration, so as to equalize solute concentrations on both sides of the membrane. When the skin is in direct contact with liquid after urination, the agent dissolved in the urine will cause water to diffuse from the skin cells of the wearer into the urine outside of the body, thus reducing skin hydration.

Osmolality changing agents include those that ionize like NaCl, $CaBr_2$, KCl, $CaCl_2$, LiCl and NaBr as well as those that do not, like methanol, urea, dextrose and glycerol. The amount of a chosen agent that will change the osmolality of a solution to above about 300 mOs/kg will vary with the particular agent. Necessary concentrations of exemplary osmolality changing agents in an aqueous solution in weight percent are, for example, $CaCl_2$, 1.5; NaCl, 1; D-fructose 5.5; D-glucose (dextrose), 5; $NaHCO_3$, 3; glycerol, 3; methanol, 1; LiCl, 0.75; urea, 2; KCl, 1.5; and NaBr, 2 (CRC Handbook of Chemistry and Physics, $57^{th}$ edition, 1976–1977, published by CRC Press, Cleveland, Ohio, at pages D218–267). It should be noted that these concentrations are based on solutions in water.

In order to calculate the number of grams of osmolality changing agent needed in a particular personal care product, some estimates or assumptions must be made regarding the amount of urine the product will receive over its useful life. In the case of diapers, for example, since a baby can deliver an amount of urine up to about 100 ml per urination, a value representing four rather large urinations (a total of 400 mls of urine) is probably a good "worst case" estimate. It is then a simple matter to calculate the number of grams of osmolality changing agent needed. E.g., for NaCl, since a 1 weight percent solution is needed, 4 grams of NaCl per 400 mls of water would be needed. For glycerol, for example, this amount would be 12 grams. It should be remembered, however, that these amounts are based on increasing the osmolality of the fluid in the personal care product to the minimum of 300 mOs/kg. Greater amounts of the osmolality changing agent in a product would give greater reduction in skin hydration, as shown in the testing below, making these estimated amounts lower bounds or minimums. Actual amounts of osmolality changing agent added to a personal care product for commercial purposes could be many times the minimum calculated here in order to deliver even greater reductions in skin hydration. Amounts of about 500 mOs/kg, 1000 mOs/kg or greater could be used with amounts of 1000 mOs/kg or more preferred.

The agent for use in this invention is preferably amenable to use in continuous fiber production processes like airforming, meltblowing, spunbonding, bonding and carding and airlaying. In this manner, it may be incorporated into current converting processes with little adjustment and used in virtually any of the layers of personal care products currently made. If in particulate form, an agent could be attached to the fibers of a web like the liner or to a superabsorbent/pulp layer through the use of an adhesive or binder or added to the fiber as long as it could get into solution with the melt spinning polymers. If the fibers were meltspun, particulate osmolality changing agents could be added to the fibers as they were produced, adhering to the semi-molten fibers and remaining there after the fibers completely cooled. If the osmolality changing agent were a liquid, it could be sprayed on the web, or the web dipped into the agent, after production.

In order to test the invention, armband skin hydration testing was performed. In one experiment, the armband had an absorbent of fluff placed between the arm and the band. A normal saline solution of 0.9 weight percent sodium chloride was added to the absorbent of a first (control) armband at the volume of 6 grams of fluid per gram of absorbent. A saline solution of 7.4 weight percent of osmolality changing agent sodium chloride was added to the absorbent of a second armband at the same addition volume. The surface tension of both solutions was adjusted to about 55 dynes/cm. After an hour, the skin hydration was measured and found to be 1.73 $g/m^2$ in two minutes for the control and 1.24 $g/m^2$ in two minutes for the high saline armband, a reduction of 28 percent. This experiment was repeated on a different subject and skin hydration was found to be 1.4 $g/m^2$ in two minutes for the control and 0.97 $g/m^2$ in two minutes for the high saline solution, a reduction of 30 percent.

In a second experiment, a control as above was used as well as an armband in which 8.52 grams of osmolality changing agent sodium chloride was added to the target area. Water was added to each armband and after an hour the control had a skin hydration of 1.62 $g/m^2$ in two minutes versus 1.13 $g/m^2$ in two minutes for the sample, a reduction of 30 percent. Reductions in skin hydration of 10, 20 or other varying percentages can therefore be achieved by varying the amount of osmolality changing agent added to the product.

It is thus shown that placing an osmolality changing agent in close proximity to the skin can significantly reduce skin hydration. This reduced skin hydration is believed to result in reduced skin redness and irritation.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means plus function claims are intended to cover the structures described herein as performing the recited function and not only structural equivalents but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

What is claimed is:

1. A personal care product comprising an osmolality changing agent that will increase the osmolality of an aqueous solution of at least about 10 ml to above about 300 milliosmoles per kilogram.

2. The personal care product or claim 1 wherein said osmolality changing agent will increase the osmolality of an aqueous solution to above about 1000 milliosmoles per kilogram.

3. The personal care product of claim 1 wherein said osmolality changing agent is selected from the group consisting of NaCl, LiCl, $CaCl_2$, $NaHCO_3$, KCl, NaBr, D-fructose, dextrose, methanol, urea and glycerol.

4. The personal care product of claim 1 selected from the group consisting of diapers, training pants, absorbent underpants and adult incontinence products.

5. The product of claim 4 wherein said personal care product is an adult incontinence product.

6. The product of claim 4 wherein said personal care product is a diaper.

7. A diaper comprising an osmolality changing agent that will increase the osmolality of an aqueous solution to above about 300 milliosmoles per kilogram, wherein said osmolality changing agent is NaCl in an amount of at least 4 grams.

8. A diaper comprising an osmolality changing agent that will increase the osmolality of an aqueous solution to above about 300 milliosmoles per kilogram, wherein said osmolality changing agent is glycerol in an amount of at least 12 grams.

9. The product of claim 4 wherein said personal care product is a training pant.

10. A skin hydration reduction system for personal care products comprising an osmolality changing agent that will reduce skin hydration in an armband test by at least 10 percent.

11. The skin hydration reduction system of claim 10 for that will reduce skin hydration in an armband test by at least 20 percent.

12. A skin hydration reduction system for personal care products comprising an osmolality changing agent that will reduce skin hydration in an armband test by at least 30 percent.

13. The skin hydration reduction system of claim 10 wherein said osmolality changing agent is located within fibers.

14. The skin hydration reduction system of claim 10 wherein said osmolality changing agent is attached to the fibers of a web.

15. The skin hydration reduction system of claim 14 wherein said osmolality changing agent is attached to the fibers of a web with an adhesive or binder.

* * * * *